United States Patent [19]

Barbetti

[11] Patent Number: 4,959,354
[45] Date of Patent: Sep. 25, 1990

[54] MIXTURES OF FSH AND LH FROM PIG HYPOPHYSES IN A DEFINITE RATIO

[75] Inventor: Manlio Barbetti, Rome, Italy

[73] Assignee: Istituto Farmacologico Serono S.P.A., Italy

[21] Appl. No.: 73,901

[22] Filed: Jul. 14, 1987

Related U.S. Application Data

[63] Continuation of Ser. No. 834,141, Feb. 24, 1986, abandoned, which is a continuation of Ser. No. 578,517, Feb. 1, 1984, abandoned.

[30] Foreign Application Priority Data

Feb. 11, 1983 [IT] Italy .............................. 47699 A/83

[51] Int. Cl.$^5$ ...................... A61K 37/36; A61K 35/55
[52] U.S. Cl. .................................... 514/21; 424/565; 530/398; 514/8
[58] Field of Search .......................... 424/108; 514/21; 530/398

[56] References Cited

U.S. PATENT DOCUMENTS

| 2,030,209 | 2/1936 | Hisaw et al. | 424/108 |
| 2,356,802 | 8/1944 | van Dyke et al. | 314/5 |
| 4,115,375 | 9/1978 | Pedersen | 530/398 |
| 4,780,451 | 10/1988 | DOnaldson | 514/12 |

FOREIGN PATENT DOCUMENTS

| 197709 | 11/1977 | U.S.S.R. | 424/108 |
| 1065127 | 4/1967 | United Kingdom | 530/398 |

OTHER PUBLICATIONS

Elsden et al., *Theriogenology* 1978 9(1), cited in Chem. Abstracts vol. 88:131270C 1978.
Remingtons Pharmaceutical Sciences, 15th ed. 1975 p. 883.
Lauria et al., "Superovulation of Dairy and Beef Cows . . ." Theriogenology, vol. 20, No. 6, 1983, pp. 675–682. Abstract presented the Tenth Intl'l Congress of Animal Reproduction and Artificial Insemmination, June 10–14, 1984.
"Superovulation in Cattle, Dose Response to FSH-W . . .", by Donaldson, Theriogenology 23:189 (1985).
"Dictionnaire Vidal", 1967, O.V.P., Paris. p. 610, item: "Gonadormone".
Chemical Abstracts, vol. 102, No. 13, Apr. 1, 1985, p. 91, "Application of LH/FSH-RH (Receptal) for Induction Ovulation in Sows"; & Veterinaria (Sarajevo) 1983,32(1), 63–71.
Chemical Abstracts, vol. 100, No. 13, Mar. 26, 1984, p. 98, "Superovulation of Diary and Beef Cows . . ." Theriogenology 1983, 20(6), 675–682.
Chemical Abstracts, No. 1, Jan. 1, 1979, p. 98, "Superovulation, Ferilization and Embryo Recovery . . . "; Theriogenology 1978, 19(2–3), 167–174.
English translation of Japanese article, "Biochemical Information Transmitter-Peptide Amine", pp. 78–88, by Yajima et al., Jan. 10, 1983.
Investigation of Factors Affecting Superovulation and Non-Surgical Embryo Recovery from Lactating British Friesian Cows, Newcomb, The Veterinary Record, Jan. 19, 1980, pp. 48–52.
Superovulating Cows with Follicle Stimulating Hormone and Pregnant Mare's Serum Gonadotrophin, Elsden et al., Theriogenology, Jan. 1978, vol. 9, No. 1, pp. 17–26.
Superovulation of Cattle with Pregnant Mare's Serum Gonadotrophin and Follice Stimulating Hormone, Seidel, Jr. et al., Control of Reproduction in the Cow, Sreenan, Editor, 1978.
Antagonistic Effect of LH on FSd-Induced Superovulation in Cattle, Chupin et al., Theriogenology, Jan. 1984, vol. 21, No. 1, p. 229.
Use of Pituitary FSH to Induce Superovulation in Cattle: Effect of Injection Regimen, Chupin et al., Theriogenology, Jan. 1982, vol. 17, No. 1, p. 81.
Efficacy of Shortened FSH Treatment for Superovulating Cattle, Garcia et al., Theriogenology, Jan. 1982, vol. 17, No. 1, p. 90.
Comparison of Follicle Stimulating Hormone (FSH) in Gelatin and Saline Diluents for Superovulating Donor Cattle, Theriogenology, Jan. 1982, vol. 17, No. 1, pp. 97.
The Effect of FSH on Sperm Transport in Cattle, Wilet et al., Theriogenology, Jan. 1982, vol. 17, No. 1, p. 113.
Lauria, A., Oliva, O., Genazzani, A. R., Cremonesi, F., Crottis, S., Barbetti, M., Improved Method to Induce Superovulation in Cattle Using Human Menopausal Gonadotropin (hMG). Theriogenology, 18: 357–364 (1982).
Greve, T., Bovine Egg Transplantation in Denmark. Carl Fr. Mortenses A/S. Copenhagen, p. 130 (1981).
Betteridge, K. J., Techniques and Results Obtainable in Embryo Transfer. In: Embroy Transfer in Farm Animals, Ed. K. J. Betteridge, Canada Dept. of Agric. Monograph 16, p. 7 (1977).
C. Polge, B. N. Day and T. W. Groves, "Synchronisation of Ovulation and Artifical Insemination in Pigs", The Veterinary Record, Aug. 10, 1968, pp. 136–142.
Translation of Reference L/"197709", Nov. 14, 1977, Soviet Union, 'Animal Husband Res'.
The Merck Index, Ninth Edition, p. 980.
"Influence of Differences in the Persistance of Luteinizing Hormones . . ." by Albert F. Parlow, Endocrinology, vol. 97, 1109–1110 (1972).
"Species Differences in Follicle Stimulating Hormone . . . " by ALbert F. Parlow, Endocrinology, vol. 73, July–Dec. 1963, 740–743.

*Primary Examiner*—Delbert R. Phillips
*Attorney, Agent, or Firm*—Ostrolenk, Faber, Gerb & Soffen

[57] ABSTRACT

The mixturex of FSH (follicle stimulating hormone) and LH (luteinizing horomone) being extracted from pig hypophyses in a definite ratio, improve to an optimum level the induction of super-ovulation in bred animals.

7 Claims, No Drawings

MIXTURES OF FSH AND LH FROM PIG HYPOPHYSES IN A DEFINITE RATIO

This is a continuation of Application Ser. No. 834,141 filed on Feb. 24, 1986 which was a continuation of application Ser. No. 578,517, filed Feb. 9, 1984, now abandoned.

The multiple ovulation, or super-ovulation, induced in cattle, goats and sheep, is a basic point, in order to obtain certain goals of the utmost interest for the agricultural economy: programmed pregnancies, twin pregnancies and especially the embryonal transplant.

In the bred animal species the embryonal transplant serves to obtain, from a particularly gifted female (for instance: a high production of milk) a maximum quantity of ovules being fertilized with sperm of selected males. These genetically superior embryos are transplanted into other animals which are able to carry out the pregnancy to the end.

Schematically, the embryo transplant may be subdivided into two steps:

during the first step one induces, in the 'donor' female, by means of the administration of gonadotropins, the maturation of several follicles instead of the one follicle which comes to maturation spontaneously.

during the second step, the morphologically normal embryos, which have been collected in the genital tract of the animal having been previously treated with gonadotropins, and later submitted to an artificial insemination, are transplanted into other females having been "syncronized" and being called the "receivers".

The result of the super-ovulation does not reach, in several cases, a good economic result, due to the following reasons:

(a) formation of too scarce a number of embryos, or/and formation of anomalous embryos being unable to survive;

(b) induction of ovaric injuries capable of hindering subsequent super-ovulations in the females which are genetically superior.

There is general agreement on the fact that the hormonal stimulation procedure for several follicles requires the most careful adjustment and tuning.

The multiple ovulation, or super-ovulation, is normally induced by means of the administration, either of PMSG (Pregnant Mare Serum Gonadotropin) having been extracted from the blood of a pregnant mare, or otherwise of FSH (Follicle Stimulating Hormone) having been extracted from the hypophyses of bred animals, such as pigs and horses.

PMSG has had for many years a dominant position in the super-ovulation of all bred animals, owing to its large availability together with its easy administration. This hormone, consisting of one molecule only which has joint activities of the FSH type and of the LH type, has a very high content of n-acetyl-neuraminic acid and remains in the circulation for many days after one injection only. Therefore it is possible, with PMSG, to obtain a satisfactory stimulation by means of the administration of the usual dosage in one injection only.

However, the responses to the super-ovulating treatments made with PMSG are too variable, even when the use of the hormone is performed within exact programs and terms.

Moreover, the PMSG produces some alterations of the ovaric structures, which are evident, after administration, by long delays in recurrence of the spontaneous cycles. These delays are much longer than those resulting from super-ovulating treatments with other kinds of Gonadotropins.

It appears that even the lengthy presence of PMSG in the circulation could be the cause of some undesirable effects, such as the variable response, and the production of a high percentage of abnormal embryos.

For the above mentioned reasons, there is now a trend to replace PMSG by FSH, extracted from the hypophyses of bred animals. According to what is known from literature, the product most in use is FSH-P, consisting of an FSH extracted from pig hypophyses and whose dosage is made in eq. mg of the standard Armour FSH.

The American patent No. 2,799,621 (1957) issued to Armour, states that FSH obtained according to the process as described in it is particularly useful because it is essentially devoid of LH. Moreover, the patent states that this fact is, in itself, an important discovery, because FSH has some applications wherein the substantial lack of the LH is useful.

From all the recently issued literature it results that the administration scheme actually preferred consists of the administration of 30 to 32 mg of FSH-P, without any addition of LH, over a period of 5 days.

The main purpose of the present invention is a composition of FSH and LH being extracted from pig hypophyses, in a definite ratio, giving results which are superior to those obtained both with FSH-P and with PMSG, in inducing super-ovulation in bred animals.

Another purpose of the present disclosure is to provide a method to induce super-ovulation in bred animals, by administering to said animals the above mentioned composition of FSH and LH. Other purposes of the discovery shall be evident from the following description.

The FSH/LH ratio, in the composition made according to the present disclosure, is contained between 0.5 and 2.5 when the dosage of FSH and of LH is performed respectively with the Steelman and Pohley (Steelman S. L. and Pohley F. M.—Endocrinology 53: 604.1953) and with the Parlow methods (Parlow A. F. in Albert A. (ed.) Human Pituitary Gonadotropins 300–310—C. C. Thomas, Springfield, Ill.), using as reference preparation the 1st hMG International Standard for biological dosages of FSH and LH.

The method to extract and refine the FSH/LH composition being produced from pig hypophyses according to the present disclosure is described in detail as follows.

The raw material used in this process consists preferably of frozen hypophysis glands of pigs, which must be carefully collected and stored.

In the normal process of the industry, the extracts are separated from the residue or insoluble part by means of centrifugation, although other separation methods may of course be used. In the same way, the dialysis may be replaced by ultra-filtering methods.

All stages of the method must be carried out at a sufficiently low temperature, in order to prevent denaturation of the gonadotropins. Temperatures under 10° C. are usually advised. The frozen pig hypophyses are thawed at 4° C. in acetone containing phenyl-methane-sulphonyl-fluoride, and then homogenized.

The homogenized material is filtered, washed several times with acetone, pre-cooled, and dried under vacuum, in order to obtain an acetonic dust.

The acetonic dust is added to the acetate-ethanol buffer precooled at 4° C., pH5, containing 40% of ethanol and phenyl-methane-sulphonyl-fluoride. The mixture is stirred for 20 hours at 4° C. The centrifugation of the extracted product with acetate-ethanol gives a clear supernatant which is adjusted to an ethanol content of 80%. The precipitate so obtained is collected by decanting and centrifugation.

Later an extraction in an ammonium bicarbonate solution is carried out in order to eliminate the insoluble proteins, then the insoluble residue is removed by centrifugation, the supernatant is dialyzed against water and then lyophilized, in order to obtain raw porcine gonadotropins.

A solution of raw material is prepared in distilled water, and adjusted to 5.3 pH and to 30% saturation with ammonium sulphate. The precipitate obtained is removed by centrifugation and the supernatant adjusted to 7.3 pH and to 50% saturation with ammonium sulphate.

The precipitate, containing the greatest part of LH, is later collected by means of centrifugation, dialysed against water and then lyophilized. This fraction, later indicated as "LH fraction", contains also some small quantities of FSH.

The ammonium sulphate concentration of the supernatant is then adjusted to 90% saturation, and the mixture is left at rest for several hours. The precipitate, rich in FSH, is collected, dialyzed and lyophilized. This fraction, to be indicated later as "FSH fraction", also contains some small quantities of LH.

The "FSH fraction" and the "LH fraction" obtained by the method described above are contaminated, respectively, by minor quantities of LH and FSH. The entity of contamination varies from one preparation to the other, and must be exactly determined in both fractions, in order to calculate the quantities required to obtain a mixture with the desired composition of FSH and of LH.

The starting materials to prepare a mixture of FSH and LH in a definite ratio are:

"FSH fraction" containing "a" International Units of FSH per mg, and "b" International Units of LH per mg.

"LH fraction" containing "c" International Units of FSH per mg and "d" International Units of LH per mg.

The "x" and "y" quantities, expressed in milligrams, respectively for the "FSH fraction" and the "LH fraction" to be included in the mixture in order to obtain a composition containing "T" units of FSH and an FSH/LH ratio="R" result from the following formulae:

$$x = \frac{T}{R} \cdot \frac{c - R \cdot d}{b \cdot e - a \cdot d}$$

$$y = \frac{T}{R} \cdot \frac{R \cdot b - a}{b \cdot e - a \cdot d}$$

For instance, "x" milligrams of an "FSH fraction" containing 27.3 Int. Units of FSH per milligram, and 6.73 Int. Units of LH per milligram, must be mixed with "y" milligrams of an "LH fraction" containing 8.9 Int. Units of FSH per milligram and 811.7 International Units of LH per milligram, in order to obtain "T"=120,000 Int. Units of FSH with a ratio ("R") FSH/LH.=1

By applying the above, one has:

$$x = \frac{120,000}{1} \cdot \frac{8.9 - 1 \cdot 811.7}{6.73 \cdot 8.9 - 27.3 \cdot 811.7} = 4359.2$$

$$y = \frac{120,000}{1} \cdot \frac{1 \cdot 6.73 - 27.3}{6.73 \cdot 8.9 - 27.3 \cdot 811.7} = 111.7$$

Therefore, 4359.2 mg of the "FSH fraction" must be mixed with 111.7 mg of the "LH fraction" in order to obtain a composition containing 120,000 International Units of FSH and 120,000 International Units of LH (ratio FSH/LH=1).

The induction of a super-ovulation in order to obtain from a donor female a maximum quantity of live and transplantable embryos was and is now the target, with hormones and administration schedules of various kinds, in all the bred animals. Recently, to the above mentioned breeds, also animals used in pharmacological research, such as monkeys, dogs and cats, have been included.

However, some statistically convalidated results are available only for cows, as it results from the general review on the subject published in 1977, by the Department of Agriculture of Canada (Betteridge K. J., Editor, 1977, Canada Department of Agriculture, Monograph 16).

Calculations based on more than 1700 donor cows indicate that the yield of transplantable embryos, although extremely variable, is, on an average, under 5 per animal. (Moor R. M. et al., Vol. i, page 43, 9th International Congress on Animal Reproduction and Artificial Insemination—Madrid 1980).

The composition according to the present invention has been tested in the bovine species, with results far superior to the above indicated average.

A schedule of treatment with mixtures of FSH and LH prepared in accordance with the present invention and suitable for Frisian cows in the full milk producing period, consists of the administration of a total of 1000 International Units of FSH and 1000 Int. Units of LH in decreasing dosages, over a period of 5 days starting from the 9th to 11th day of the estral cycle.

On the evening of the third day of treatment, 1 ampoule of Prostaglandin is administered in order to provoke luteolysis. Two or three artificial insemination are made, starting 12 hours from the onset of the estral period.

On the seventh day after the second insemination, the embryos are removed, in a non-surgical way, by washing the uterine horns.

With this system all embryos resulting from the fertilization of the ovuli produced, as well as the non fertilized ovuli, if any, are collected in a container. The collected embryos are carefully examined under the microscope and subdivided, according to their morphological features, into transplantable and non-transplantable embryos. In Frisian cows during their milk producing period, treated with the above mentioned program, the following average figures are obtained:

total embryos $\bar{x} = 14.571$ transplantable embryos $\bar{x} = 11.142$

In the meat producing breeds, such as "marchigiane" or "chianine", a total dosage of 750 Int. Units of FSH and 750 Int. Units of LH is sufficient.

The administration program of this dose, and every other detail of the treatment, is identical to that already described for the Frisian cows in the milk producing period.

In the "marchigiane" and "chianine" cows, the following averages are obtained:

$$\text{total embryos } \bar{x} = 14.142$$

$$\text{transplantable embryos } \bar{x} = 10.571$$

It is very important to emphasize, that the above reported average figures result from the treatment of animals "on the field".

It is well known to the experts, that the results are considerably improved when treatment is made, instead of "on the field", in a specialized Clinic, where all the animals may be treated in full respect of all technical conditions.

I claim:

1. A method of inducing superovulation in cows which comprises administering thereto a superovulation effective amount of a gonadotropin composition comprising a mixture of porcine FSH and porcine LH in an IU ratio of between 0.5 and 2.5.

2. The method of claim 1, wherein said IU ratio is about 1.

3. The method of claim 2, wherein said gonadotropin composition is administered over a period of 5 days from the 9th to the 11th day of the estral cycle.

4. In a method of inducing superovulation in cows by administering gonadotropins thereto, the improvement which comprises employing a mixture of FSH and LH extracted from pig hypophyses in an IU ratio of between 0.5 and 2.5 as the gonadotropins.

5. In a method of inducing superovulation in cows by administering gonadotropins thereto, the improvement which comprises employing a mixture of FSH and LH extracted from pig hypophyses in an IU ratio substantially equal to 1 as the gonadotropins.

6. A composition comprising a mixture of porcine FSH and porcine LH in an IU ratio of between 0.5 and 2.5.

7. The composition of claim 6, wherein said IU ratio is about 1.

* * * * *